United States Patent [19]
Leighton et al.

[11] Patent Number: 6,057,458
[45] Date of Patent: May 2, 2000

[54] PRODUCTION OF 3-ALKOXYALKANALS BY HYDROFORMYLATION OF ENOL ETHER SUBSTRATES

[75] Inventors: James L. Leighton; Deidre N. O'Neil, both of New York, N.Y.

[73] Assignee: The Trustees of Columbia University in the City of New York, New York, N.Y.

[21] Appl. No.: 08/969,178

[22] Filed: Nov. 12, 1997

[51] Int. Cl.$^7$ .................................................. C07D 319/06
[52] U.S. Cl. .......................................................... 549/375
[58] Field of Search ............................................ 549/375

[56] References Cited

U.S. PATENT DOCUMENTS

| | | | |
|---|---|---|---|
| 4,772,625 | 9/1988 | Brewster et al. | 514/452 |
| 5,449,793 | 9/1995 | Miyazawa et al. | 549/373 |
| 5,530,150 | 6/1996 | Takaya et al. | 556/18 |
| 5,563,295 | 10/1996 | Takaya et al. | 562/606 |
| 5,631,345 | 5/1997 | Takaya et al. | 528/392 |

OTHER PUBLICATIONS

Agbossou, F. et al. (1995) "Asymmetric Hydroformylation," *Chem. Rev.*, 95: 2485–2506.

Amer, I. and Alper, H. (1990) "Zwitterionic Rhodium Complexes as Catalysts for the Hydroformylation of olefins," *J. Am. Chem. Soc.*, 112:3674–3676.

Beller, M. et al. (1995) "Progress in Hydroformylation and Carbonylation," *J. Mol. Catal. A*, 104:17–85.

Botteghi, C. et al. (1987) "Advances in the Hydroformylation of Olefins Containing Functional Groups," *G. J. Mol. Catal.*, 40:129–182.

Buisman, G.J.H. et al. (1995) "Hydridorhodium Diphosphite Catalysts in the Asymmetric Hydroformylation of Styrene," *J. Chem. Soc. Dalton Trans.*, 409–417.

Casey, C.P. et al. (1992) "Diphosphines with Natural Bite Angles near 120; Increase Selectivity for n–Aldehyde Formation in Rhodium–Catalyzed Hydroformylation," *J. Am. Chem. Soc.*, 114:5535–5543.

Jongsma,T. et al. (1991) "A Mechanistic Study of Rhodium tri(o–t–butylphenyl)phosphite complexes as Hydroformylation Catalysts," *J. Organomet. Chem.*, 421: 121–128.

Kennedy, R. M., et al. (1988) "A Synthesis of 19–Dehydro-amphoteronolide B," *Tetrahedron Lett.*, 29: 451–454.

Kollar, L. et al. (1993) "Highly Stereoselective Hydroformylation of a (2R)–2–tert–butyl–Δ$^4$–1,3–oxazoline Derivative," *J. Organomet. Chem.*, 445: 257–259.

Lazzaroni, R.; Settambolo, R.; Uccelo–Barretta, G. (1995) "β–Hydride Elimination and Regioselectivity in the Rhodium–Catalyzed Hydroformylation of Open Chain Unsaturated Ethers," *Organometallics*, 14: 4644–4650.

Lazzaroni, R.; Pucci,S.; Bertozzi, S.; Pini, D. (1983) "Diastereoselectivity in the Rhodium–Catalyzed Hydroformylation of (+) (R)–1–Phenylethyl Vinyl Ether," *J. Organomet. Chem.*, 247: C56–C58.

Mori, Y. et al. (1994) "Total Synthesis of the Polyene Macrolide Roxaticin," *Tetrahedron Lett.*, 35: 6503–6506.

Nicolaou, K. C. et al. (1988) "Total Synthesis of Amphotericin B. 3. The Final Stages," *J. Am. Chem. Soc.*, 110: 4696–4705.

Polo, A. et al. (1992) "Regioselective Hydroformylation of Cyclic Vinyl and Allyl Ethers with Rhodium Catalysts–Crucial Influence of the Size of the Phosphorus Cocatalyst," *Organometallics*, 11: 3525–3533.

Polo, A. et al. (1992) "Hydroformylation of Glucal Derivatives with Rhodium Catalysts—Crucial Influence of the Auxiliary Ligand Tris(ortho–tert–butylphenyl) Phosphite," *S. J. Chem. Soc., Chem. Commun.*, 639–640.

Poss, C. S. et al. (1993) "Two–Directional Chain Synthesis: An Application to the Synthesis of (+)–Mycoticin A," *J. Am. Chem. Soc.*, 115: 3360–3361.

Sakai, N. et al. (1993) "Highly Enantioselective Hydroformylation of Olefins Catalyzed by New Phosphinephosphite–Rh(I) Complexes," *J. Am. Chem. Soc.*, 115: 7033–7034.

Seebach, D. et al. (1988) "Totally Stereoselective Additions to 2,6–Disubstituted 1,3–Dioxin–4–ones (Chiral Acetoacetic Acid Derivatives): Synthetic and Mechanistic Aspects of Remote Stereoselectivity," *J. Am. Chem. Soc.*, 110: 4763–4772.

Van Leeuwen, P.W.N.M. & Roobeek, C. F. (1983) "Hydroformylation of Less Reactive Olefins with Modified Rhodium Catalysts," *J. Organomet. Chem.*, 258: 343–350.

*Primary Examiner*—Ba K. Trinh
*Attorney, Agent, or Firm*—John P. White; Cooper & Dunham

[57] ABSTRACT

The present invention provides a process for producing an optically active aldehyde which comprises hydroformylating a terminal olefin substrate represented by the formula:

$$Q_1Q_2C=CH_2$$

wherein $Q_1$ is an atom or group other than carbon or hydrogen and $Q_2$ is an atom or group other than hydrogen, in the presence of CO, $H_2$ and a catalyst, which catalyst comprises a transition metal based compound and a ligand.

14 Claims, 9 Drawing Sheets

PRODUCTION OF 3-ALKOXYALKANALS BY HYDROFORMYLATION OF ENOL ETHER SUBSTRATES

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

The development of reliable asymmetric catalysts for organic synthesis has had an enormous impact on the ability of chemists to assemble relatively small enantiopure building blocks for pharmaceutical research and natural products synthesis. (Noyori, 1994). Many such processes are now amenable to industrial-scale production. By contrast, similarly reliable catalytic methods for stereoselective carbon—carbon bond formation during the middle and late stages of a relatively complex synthetic enterprise are perhaps not as developed, with the consequence that many worthy pharmaceutically relevant targets cannot practically be synthesized in large amounts. This is unacceptable. The recently developed HIV protease inhibitors provide a striking example of the increasing level of structural complexity that may be required of synthetic pharmaceuticals. As increasingly complex pharmaceutical agents are designed, synthetic chemists must provide the necessary tools for their efficient synthesis during the discovery and production stages. Indeed, the availability of new synthetic methods can open up new avenues in pharmaceutical research.

The recent resurgence of drug-resistant bacterial and fungal infections demands the renewed efforts of medicinal and synthetic chemists alike in antibiotics research. (Sternberg, 1994). The polyene macrolide antibiotics (e.g. amphotericin B and mycoticin A are a rich natural source of antibiotic lead structures. (Rychnovsky, 1995). Indeed, amphotericin B, while far from ideal, is still one of the most effective clinical anti-fungal agents known. (Belard, 1986; Hartsel, et al., 1993). This general type of structure could form the basis of the next generation of anti-fungal agents. The recent discovery of leucascandrolide A (Nakata, 1990) a powerfully anti-fungal natural product, supports this notion. While this latter compound is not a polyene macrolide, it does share one primary structural feature usually found in the polyene macrolides: an extended (1,3,5 . . . ) polyol-derived segment. Thus, the development of general methods for the synthesis of such segments that are catalytic and require only inexpensive reagents is a worthy goal whose attainment could have a wide-ranging effect on both the discovery and production stages of pharmaceutical research.

Figure 1A:
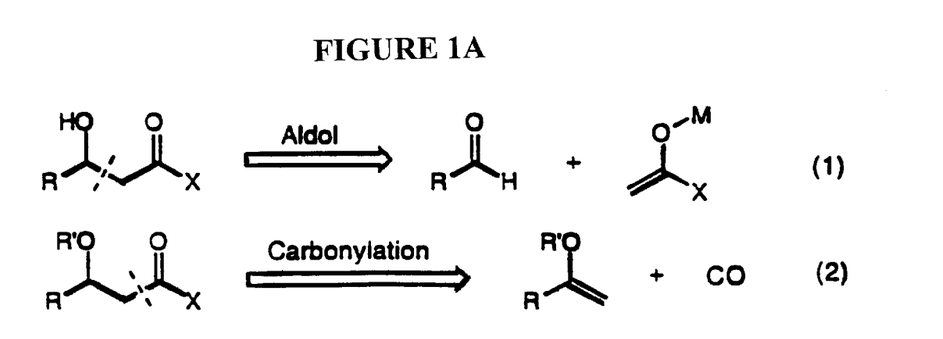
FIG. 1A. Diagramatic representation of aldol addition and carbonylation, indicating the focus on the carbonyl carbon—α-carbon bond by way of olefin carbonylation in the latter case.

Many methods have been developed for the stereoselective synthesis of (1,3,5 . . . ) polyol chains. (Rychnovsky, 1995; Oishi and Nakata, 1990). Recently successful and generally applicable methods for polyol synthesis based on dithiane-epoxide and cyanohydrin-alkyl halide couplings respectively have been developed. (Nicolaou, et al., 1988; Kennedy et al., 1988; Poss, et al., 1993; Mori, et al., 1994; Rychnovsky, et al., 1994). In devising a new approach based on catalytic processes, the present invention is focused on the β-hydroxy aldehyde as a fundamental building block. Previous methods for the synthesis of such aldehydes have relied principally on aldol addition and allylation reactions and related processes. (Carreira, et al, 1994; Evans, et al., 1996; Evans, et al., 1997; Paterson, et al., 1996; Yamamoto, et al, 1993). However, the focus of the present invention on the carbonyl carbon—α-carbon bond by way of olefin carbonylation provides a novel approach to catalytic aldol synthesis (FIG. 1A).

Figure 1B:
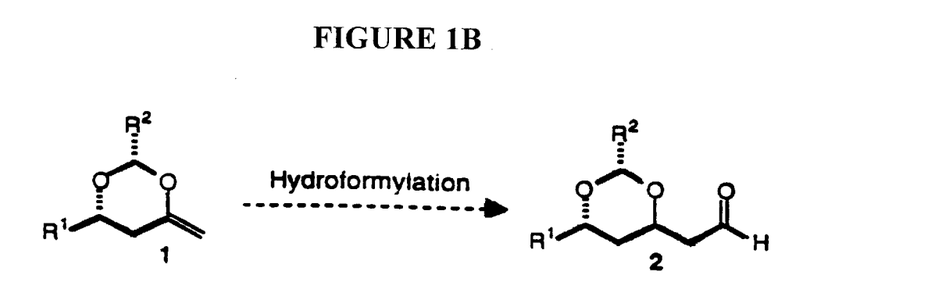
FIG. 1B. 3,5-dihydroxy aldehyde (2) produced by the hydroformylation of terminal olefin substrate (1).

These methodologies involve as the unifying theme stereo- and regioselective transition metal-catalyzed carbonylation of alkenes leading to the efficient synthesis of suitably protected/masked 3,5-dihydroxy aldehydes, extremely versatile building blocks for polyol synthesis (FIG. 1B). Focus on carbonylation derives from the observation that carbonylation is one of the most efficient and widely used processes in the chemical industry for the production of carbonyl containing compounds. (Colquhoun, et al, 1991). Thus, the development of carbonylation-based methods for the synthesis of (1,3,5 . . . ) polyols could accrue all the advantages that render carbonylation a feasible industrial scale process. Toward this end, four criteria may be used to evaluate the development of these new synthetic methods. First, the diastereoselectivity should be high (to avoid tedious separations) and, as important, predictable. Second, the reactions should be efficient, providing high yields of the desired products with minimal waste production and minimal use of unwieldy and/or expensive reagents. Third, the reactions should be operationally simple requiring no extraordinary techniques and, ideally, requiring little or no work-up and only simple purification methods. Finally, the usefulness of the methods will be limited if the availability of the requisite starting materials is limited.

The present invention provides the basis for a comprehensive and coherent approach to the synthesis of (1,3,5 . . . ) polyol fragments and the efficient synthesis of relevant targets.

SUMMARY OF THE INVENTION

The present invention provides a process for producing an optically active aldehyde comprising hydroformylation of a terminal olefin substrate represented by the formula:

$$Q_1Q_2C=CH_2$$

wherein $Q_1$ is an atom or group other than carbon or hydrogen and $Q_2$ is an atom or group other than hydrogen, in the presence of CO, $H_2$ and a catalyst, which catalyst comprises a transition metal based compound and a ligand.

DETAILED DESCRIPTION OF THE INVENTION

The present invention provides a process for producing an optically active aldehyde which comprises hydroformylating a terminal olefin substrate represented by the formula:

wherein $Q_1$ is an atom or group other than carbon or hydrogen and $Q_2$ is an atom or group other than hydrogen, in the presence of CO, $H_2$ and a catalyst, which catalyst comprises a transition metal based compound and a ligand.

In an embodiment of this invention, the optically active aldehyde produced is represented by the formula:

wherein $Q_1$ is an atom or group other than carbon or hydrogen and $Q_2$ is an atom or group other than hydrogen.

Figures 2A, 2B:
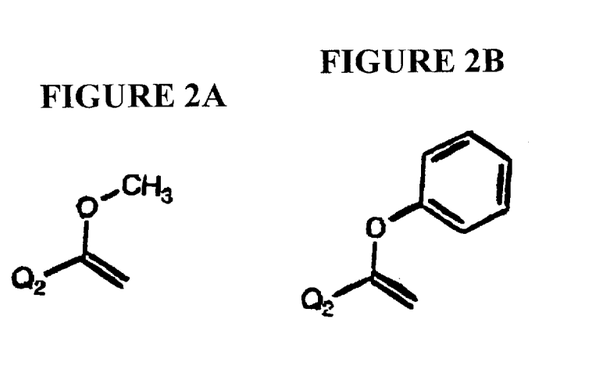
FIG. 2A. Optically active β-alkoxy-aldehyde produced is represented by the formula: $Q_1Q_2CH—CH_2—CHO$, wherein $Q_1$ represents OR, R is an alkyl group, $Q_2$ is an atom or group other than hydrogen.
FIG. 2B. Optically active β-alkoxy-aldehyde produced is represented by the formula: $Q_1Q_2CH—CH_2—CHO$, wherein $Q_1$ represents OR, R is an aryl group, $Q_2$ is an atom or group other than hydrogen.
Figure 2C:
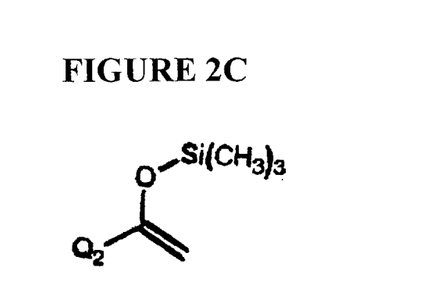
FIG. 2C. Optically active β-alkoxy-aldehyde produced is represented by the formula: $Q_1Q_2CH—CH_2—CHO$, wherein $Q_1$ represents OR, R is an trialkylsilyl group, $Q_2$ is an atom or group other than hydrogen.
Figure 2D:
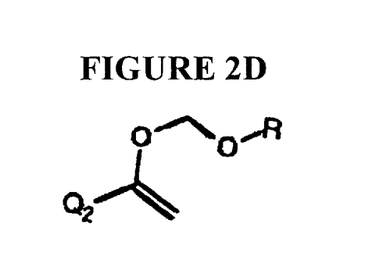
FIG. 2D. Optically active β-alkoxy-aldehyde produced is represented by the formula: $Q_1Q_2CH$—$CH_2$—$CHO$, wherein $Q_1$ represents $OCH_2OR$, R is an alkyl or an aryl group, $Q_2$ is an atom or group other than hydrogen.
Figure 2E:
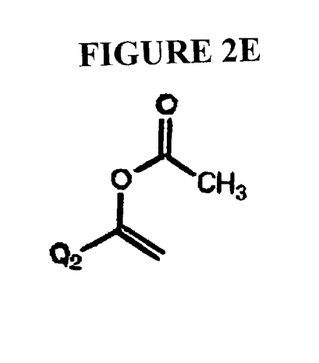
FIG. 2E. Optically active β-alkoxy-aldehyde produced is represented by the formula: $Q_1Q_2CH$—$CH_2$—$CHO$, wherein $Q_1$ represents OCOR, R is an alkyl group, $Q_2$ is an atom or group other than hydrogen.
Figure 2F:
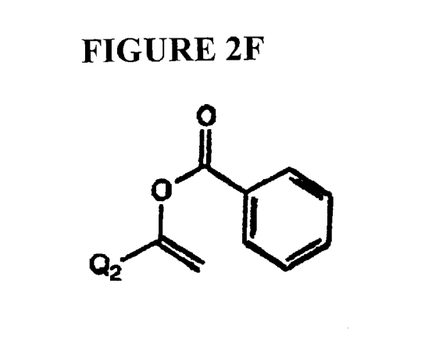
FIG. 2F. Optically active β-alkoxy-aldehyde produced is represented by the formula: $Q_1Q_2CH$—$CH_2$—$CHO$, wherein $Q_1$ represents OCOR, R is an aryl group, $Q_2$ is an atom or group other than hydrogen.

In a preferred embodiment of the present invention, $Q_1$ is represented by the formula OR, wherein R represents an alkyl group (FIG. 2A), an aryl group (FIG. 2B) or a trialkylsilyl group (FIG. 2C). In another embodiment, $Q_1$ is represented by the formula, $OCH_2OR$ wherein R represents an alkyl group or an aryl group (FIG. 2D). In another embodiment, $Q_1$ is represented by the formula OCOR wherein R represents an alkyl group or an aryl group (FIGS. 2E–2F). In another embodiment of the present invention $Q_1$ is nitrogen. In another embodiment of the present invention $Q_1$ is sulfur.

In a preferred embodiment of the present invention, $Q_2$ is carbon-based. In another embodiment of the present invention, $Q_2$ is an alkyl group, an alkoxy group, a halogen, an alkylcarbonyloxy group, a cyano group, a carboxyl group, an alkylcarbonyl group, an alkoxycarbonyl group, a phthalimido group, an acetyl group, an amino group, a benzoyl group, an acetylamino group, a benzoylamino group, an alkylamino group, a phenyl group, or a naphthyl group.

In yet another embodiment of the present invention, the terminal olefin substrate is represented by the formula:

wherein X is oxygen, nitrogen, or sulfur, $Q_1$ is an alkyl group, an acyl group, an aryl group, or an alkoxyalkyl group and $Q_2$, $Q_3$ and $Q_4$ represent any atom. In this embodiment the optically active aldehyde produced is represented by the formula:

wherein X is oxygen, nitrogen, or sulfur, $Q_1$ is an alkyl group, an acyl group, an aryl group, or an alkoxyalkyl group and $Q_2$, $Q_3$ and $Q_4$ represent any atom.

In another embodiment of the present invention, $Q_1$ and $Q_2$ are joined together in a ring structure.

In an embodiment of the present invention, the terminal olefin substrate is an enol-ether. In one embodiment of this invention, the enol-ether is 4-methylene-1,3-dioxane.

In a preferred embodiment of the present invention, the terminal olefin substrate is optically active.

In an embodiment of the present invention, the optically active aldehyde produced is a β-alkoxy-aldehyde. In an embodiment of the present invention, the optically active aldehyde produced is a 3-hydroxyaldehyde.

In a preferred embodiment of the present invention, the optically active aldehyde produced is unsubstituted at the α-carbon position. In one embodiment of the present invention, the optically active aldehyde produced is a 3,5 dihydroxyaldehyde represented by the formula:

wherein $R^1$ is an isopropyl a methyl a $BnO(CH_2)_2$, or a $(CH_3)_2C$=$C(CH_2)_5$ group and $R^2$ is a t-butyl or a methyl group.

In one embodiment of the present invention, the optically active aldehyde is produced stereoselectively. In a preferred embodiment of the present invention, the optically active aldehyde produced has more than one stereocenter. In an embodiment of the present invention, the optically active aldehyde is produced regioselectively.

In an embodiment of the present invention, the transition metal based compound comprises rhodium. In a preferred embodiment of the present invention, the transition metal based compound is $Rh(acac)CO_2$. In one embodiment of the present invention, the transition metal based compound is present at a concentration of from about 0.5 mole percent to about 2 mole percent. In another embodiment of the present invention, the transition metal based compound $(Rh_4(C))_{12}$, $[Rh(NB—D)Cl]_2$, $[Rh(COD)_2]BF_4$, $HR(CO)(P—Ph3)3$, or $RhH(CO)(PPh3)3$, or $[Rh(CO_2)_2Cl]_2$.

In an embodiment of the present invention, the ligand is optically active. In a preferred embodiment of the present invention, the ligand is a phosphine. In a preferred embodiment of the present invention, the phosphine is $PPh_3$. In another embodiment of the present invention, the ligand is a phosphite. In another embodiment of the present invention, the phosphite is $P(O-o-t-BuPh)_3$. In one embodiment of the present invention, the phosphite is present at 4.0 mole percent.

In an embodiment of the present invention, the hydroformylation is performed in a hydrocarbon solvent. In one embodiment of the present invention, the hydrocarbon solvent is benzene, ethyl benzene, hexane, or toluene. In another embodiment of the present invention, the hydroformylation is performed in an ethereal solvent. In one embodiment of the present invention, the ethereal solvent is tetrahydrofuran (THF), diethyl ether, dioxane, or t-butyl, methyl ether. In another embodiment of the present invention the solvent is ethyl acetate or dimethylformamide. While the process of the present invention is preferably performed in the presence of a reaction solvent, the process may be effected without using any reaction solvent. Where a solvent is used, any solvent may be used provided it does not adversely affect the reaction.

In an embodiment of the present invention hydroformylation is performed: (a) at a pressure of from about 25 to about 2000 psi of $H_2$:CO, (b) at a temperature of from about 25° C. to about 120° C., (c) for from about a few minutes to about several days. The reaction may be performed in a hydrocarbon, ethereal or other solvent provided it does not adversely affect the reaction. In a preferred embodiment of the present invention, hydroformylation is performed: (a) at a pressure of about 800 psi of a 1:1 mixture of $H_2$:CO; (b) at about 85° C.; (c) in a solvent comprising tetrahydrofuran; (d) for about 8 hours.

The process of the present invention may be used for the stereoselective synthesis of a (1,3,5 . . . ) polyol chain comprising use of the optically active aldehydes produced by the process of the present invention.

As used herein, the term, diastereomer refers to the optical isomer of a compound whose molecule contains more than one asymmetric atom and does not exhibit a mirror image relationship. An enantiomer exhibits the mirror image relationship. An asymmetric carbon atom is a carbon atom in union with four dissimilar atoms or groups. Compounds containing asymmetric carbon atoms are capable of existing in two optically active forms which are distinguished by being respectively levorotatory (L-form) or dextrorotatory (D-form) and also in some cases being enantiomeric. Thus, enantiomers are mirror image isomers; diastereomers are non-mirror image isomers. Molecules that are not superimposable on their mirror images are chiral. Chirality is necessary and sufficient for the existence of enantiomers. A compound whose molecules are achiral (without chirality) cannot exist as enantiomers. A racemic mixture is one in which there is a mixture of the D-form and L-form of the compound.

As used herein, the term optically active refers to isomers whose properties differ only in the direction or rotation of polarized light. Optical activity results from chirality: the non-superimposability of certain molecules on their mirror images. Optical activity is evident when a mixture contains an excess of one enantiomer, whereby an excess of the net optical rotation can be detected.

As used herein, the term regioselective refers to the selective production of branched as opposed to linear molecules including the aldehydes of the present invention. Enantioselectivity represents the maximal asymmetric induction and minimal racemization of the optically active products. Chemoselectivity refers to the preference for hydroformylation as opposed to hydrogenation. In the case of monosubstituted alkenes, enantioselection occurs only through the branched aldehyde formation.

As used herein, Ph represents a phenyl group, Me represents a methyl group, Bu represents a butyl group, Pr represents a propyl group, t-Bu represents a tert-butyl group, i-Pr represents an isopropyl group, and acac represents an acetylacetonato group.

Phosphine ligands have the general formula $PR_3$ where R is an alkyl, an aryl, H, a halide, or other related group. Phosphite ligands have the general formula $P(OR)_3$ where R is an alkyl group, an aryl group, H, a halide, or other related group. Phosphines and phosphites are neutral, two electron donors that bind to transition metals through their lone pairs. There are many examples of polydentate phosphine ligands. Chiral phosphine transition metal complexes have been synthesized which are stereogenic and can function as stereospecific catalysts. Examples of phosphine ligands include but are not limited to: $PH_3$ (phosphine), $PMe_3$ (trimethylphosphine), $PPh_3$, (triphenylphosphine), $PF_3$ (trifluorophosphine), $P(OMe)_3$ (trimethylphosphite), $P(OPh)_3$ (triphenylphosphite), $PCy_3$ (tricyclohexylphosphine), diphenylphosphinomethan (dppm), deiphenylphosphinoethane (dppe; diphos), PROPHOS, dimethylphosphinomethane (pmpm), dimethylphosphinoethane (dmpe; diphos), S,S-chiraphos, PAMP, DIPAMP, DuPHOS. Phosphines are useful ligands for transition metals. A ligand is an atom or group coordinated to a catalyst which can contribute to the compound a steric orientation or structural basis.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Example 1

Development of the Diastereoselective and Enantioselective Hydroformylation of Enol Ethers Despite the vast body of literature concerning the hydroformylation process, (Agbossou, et al., 1995; Beller, et al., 1995; Botteghi, et al., 1987) examples of enol ethers as substrates are rare. (Lazzaroni, et al, 1983; Amer, et al., 1990; Polo, et al., 1992; Polo, et al., 1992; Kollar, et al., 1993).

Figure 3A:
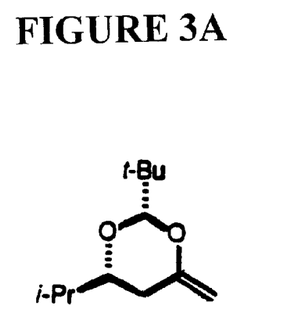
FIG. 3A. Terminal olefin substrate wherein $R^1$ is an isopropyl group and $R^2$ is a t-butyl group.
Figure 3B:
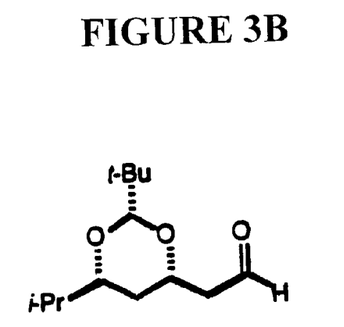
FIG. 3B. Aldehyde produced in 60% yield by hydroformylation of the substrate of FIG. 3A.
Figure 3C:
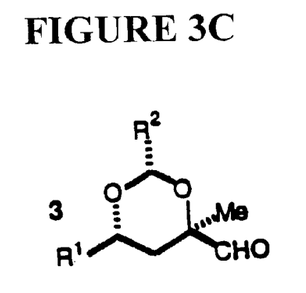
FIG. 3C. Aldehyde produced in 5% yield by hydroformylation of the substrate of FIG. 3A.
Figure 3D:
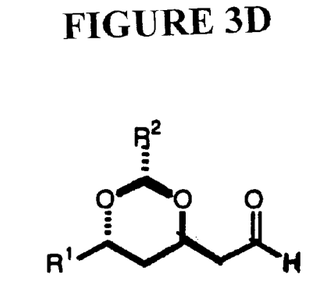
Figure 4:
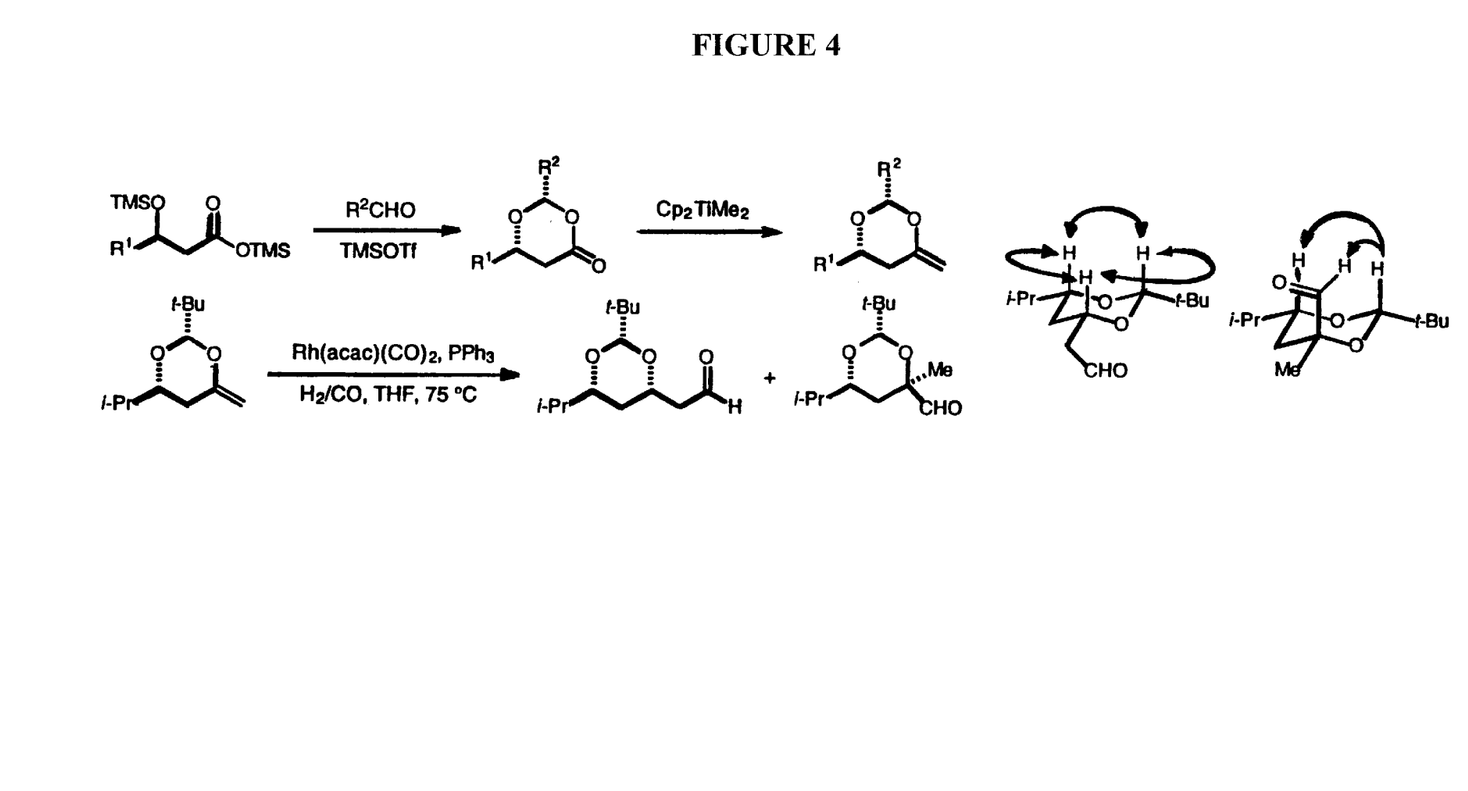
FIG. 4. Mechanistic scheme for the hydroformylation reaction.

In the case of simple vinyl ethers, the branched products (α-alkoxy aldehydes) usually predominate suggesting an electronic preference for carbonylation at the carbon bearing the oxygen. Surprisingly, there seems to be no precedent in the literature for the hydroformylation of α-alkyl substituted enol ethers. However, the electronic preference may be overridden by steric considerations as hydroformylation only rarely produces quaternary aldehydes. Taking advantage of the rigidity imposed by a cyclic system, enol ethers were prepared. Preparation of dioxanone followed the Seebach protocol (Seebach, et al, 1987) and was followed by lactone methylenation. (Petasis, et al, 1996). The terminal olefin substrate represented in FIG. 3A wherein $R^1$ is an isopropyl group and $R^2$ is a t-butyl group was subjected to hydroformylation in a stainless steel pressure vessel using 2 mole percent $Rh(acac)(CO)_2$ and 8 mole percent $PPh_3$ as the catalyst, under 800 psi 1:1 $H_2$:CO in THF at 75° C. The reaction produced an aldehyde represented in FIG. 3B in 60% yield and an aldehyde represented in FIG. 3C in about a 5% yield. No evidence for the 1,3-anti diastereomer of aldehyde 3A could be detected by $^1H$ NMR spectroscopy. The aldehyde represented in FIG. 3C was also produced diastereoselectively. Thus, although the regioselectivity is about 12:1, the overall diastereofacial selectivity is remarkably high (see FIG. 4).

Catalyst loading was dropped to 1 mole percent $Rh(acac)(CO)_2$ allowing the reactions to be generally completed in 8 hours. Use of the bulky phosphite $P(O$-o-t-$BuPh)_3$ as the ligand led to significantly faster reactions (about 45 minutes under otherwise identical conditions) in accord with earlier observations. (Van Leeuwen, 1983; Jongsma, et al., 1991). However, while the diastereoselectivity remains high, a small amount of isomerization of the olefin into the ring with this ligand was observed. Benzene, ethyl acetate (EtOAc) and tetrahydrofuran (THF) were evaluated as solvent. THF provided the cleanest reactions for the substrates tested in this experiment. Table 1 outlines results for the hydroformylation of several enol ether substrates under optimized conditions. In every case the diastereoselectivity was determined to be >50:1 based on GC analysis. Independent synthesis of the anti diastereomer of entry 3 allowed determination of a diastereoselectivity of 88:1. Among the key observations is that the bulky tert-butyl group in the acetal position is not necessary for high selectivity; indeed, no difference was observed using the corresponding acetaldehyde-derived acetal (compare Table 1, entry 2 with Table 1, entry 3). Some functional group tolerance was also demonstrated. (Table 1, entries 4 and 5). Table 1, entry 4 is especially noteworthy in the context of (1,3,5 . . . ) polyol synthesis in that a pseudo-meso synthon is produced with the termini differentiated. Finally, it was noted that the reaction is equally effective and operationally simple on a larger scale using 0.50 mole percent catalyst (Table 1, entry 3a).

In order to gain insight into the mechanism underlying the extraordinary diastereoselectivity of these reactions, it was important to determine whether insertion of the olefin into the Rh—H bond is irreversible/rate-determining. Lazzaroni documented this as the case for deuterioformylation of ethyl vinyl ether at 20° C. under phosphine/phosphite-free conditions. (Lazzaroni, et al., 1995). However, substantial incorporation of deuterium into the recovered ethyl vinyl ether was observed at 100° C. indicating that olefin insertion is reversible at this temperature. Given the moderately high temperature (75° C.) of the present reactions and the presence of $PPh_3$, the possibility that olefin insertion is fast and reversible could not be ruled out in this system. The observed selectivity could be due to a thermodynamic preference for the syn products. Deuterioformylation would not be a useful probe in this context for 1,1-disubstituted olefins.

TABLE 1

Rh-Catalyzed Hydroformylation of Enol Ethers[a]

| entry | $R^1$ | $R^2$ | major product | yield (%)[b] | rs[c] |
|---|---|---|---|---|---|
| 1 | H | t-Bu | t-Bu | 81 | 12:1 |
| 2 | Me | t-Bu | t-Bu | 72 | 13:1 |
| 3 | Me | Me | Me | 75 | 13:1 |
| 3a[d] | Me | Me | | 80 | 14:1 |

TABLE 1-continued

Rh-Catalyzed Hydroformylation of Enol Ethers[a]

$$\text{1} \xrightarrow[\substack{800 \text{ psi } 1/1 \text{ H}_2/\text{CO} \\ \text{THF, } 75^\circ \text{ C.}}]{\substack{1 \text{ mol\% Rh(acac)(CO)}_2 \\ 4 \text{ mol\% PPh}_3}} \text{2-syn}$$

| entry | R[1] | R[2] | major product | yield (%)[b] | rs[c] |
|---|---|---|---|---|---|
| 4[e] | BnO(CH$_2$)$_2$ | Me | (structure) | 71 | 9:1 |
| 5 | Me$_2$C=CH(CH$_2$)$_5$ | Me | (structure) | 71 | 11:1 |

[a]All reactions were conducted on a 2.0 mmol scale in 2.0 mL of THF.
[b]Isolated yield of major product.
[c]Regioselecitivity (2.3) determined by GC analysis of the unpurified reaction mixtures.
[d]21.5 mmol substrate. 0.50 mol % Rh(acac)(CO)$_2$, and 2.0 mol % PPh$_3$ in 20.0 mL THF.
[e]P(O-o-t-BuPh)$_3$ used in place of PPh$_3$.

Figure 5A:
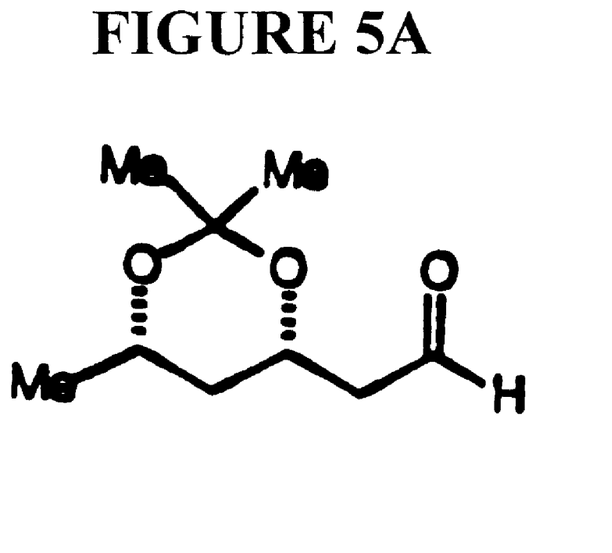
FIG. 5A. Enol ether substrate carrying acetonide protecting group used for elucidation of underlying hydroformylation mechanisms.
Figure 5B:
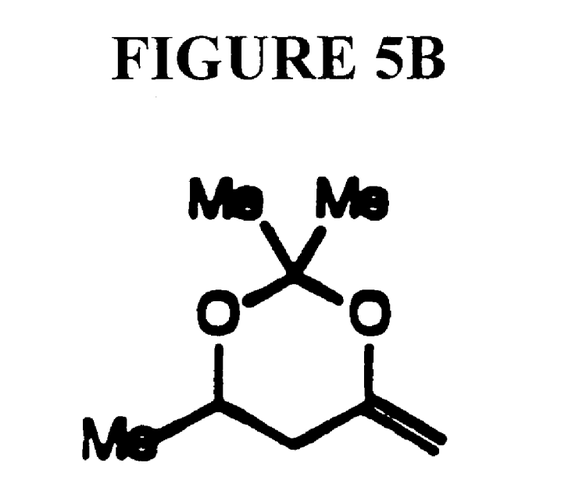
FIG. 5B. Aldehyde produced by hydroformylation of substrate 5A, indicating syn-diastereoselection despite axial methyl group.
Figure 6:
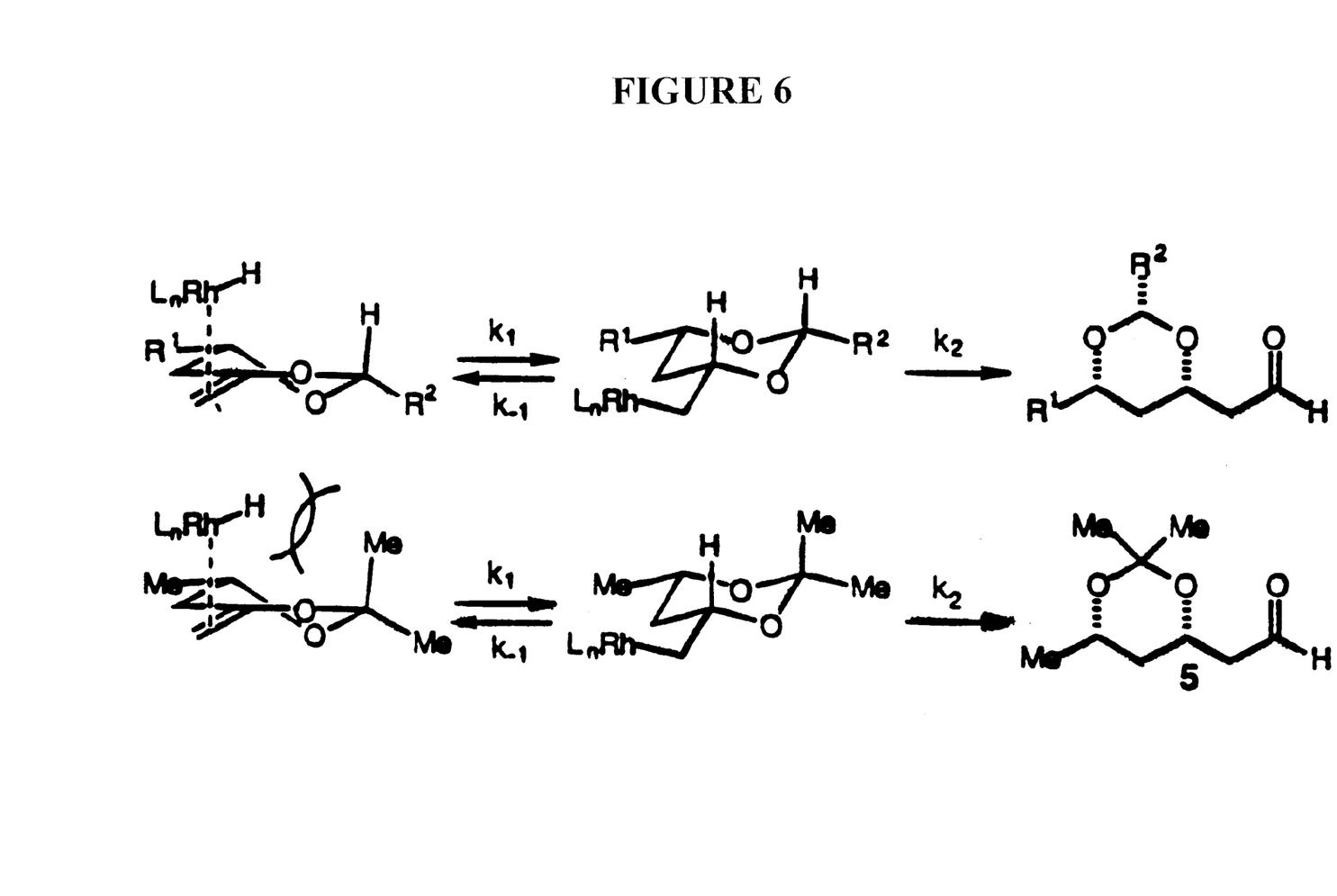
FIG. 6. Mechanistic scheme for the hydroformylation reaction of FIG. 5.

In order to distinguish between the two mechanisms, an enol ether carrying an acetonide protecting group was prepared (see FIG. 5A). After discovering that hydroformylation of this enol ether is still syn-diastereoselective, producing the aldehyde represented in FIG. 5B despite the axial methyl group (see FIG. 6) the rate of the reaction was analyzed. The presence of the axial methyl group should have a deleterious effect on the rate of hydroformylation relative to enol ethers only if olefin insertion is rate-determining ($k_2 \gg k_1$), and little or no effect if olefin insertion is fast and reversible and some part of $k_2$ is rate-determining. Table 2 outlines the results of a competition experiment between enol ether substrates (see Table 1) that was analyzed after 2 hours. It is clear that the axial methyl group does indeed have a significant effect on the rate of hydroformylation. This result is most consistent with rate-determining olefin insertion, and by extension that the observed diastereoselectivity is kinetically determined in the olefin insertion step.

TABLE 2

Competition Experiment[a]

$$\text{1b + 1c + 4} \xrightarrow[\substack{800 \text{ psi } 1/1 \text{ H}_2/\text{CO} \\ \text{THF, } 75^\circ \text{ C., 2h}}]{\text{Rh(acac)(CO)}_2, \text{PPh}_3} \text{Aldehydes}$$

| Substrate | 1b | 1c | 4 |
|---|---|---|---|
| Conversion (%)[b] | 61 | 59 | 9 |

[a]Experiment performed with 0.67 mmol of each enol ether in 2.0 mL THF. 1.0 mol % (overall) Rh(acac)(CO)$_2$, and 4.0 mol % PPh$_3$.
[b]Converions measured by GC analysis of the unpurified reaction mixture using decane as an internal standard.

Discussion

Rhodium catalyzed hydroformylation of 4-methylene-1,3 dioxanes proceeds with good regioselectivity and high diastereoselectivity. Direct production of suitably protected 3,5-dihydroxyaldehydes without the need for functional group manipulation make this an attractive synthetic method.

For certain substrates this reaction meets three critical criteria: (1) the reactions are extremely diastereoselective (>50:1), (2) they are efficient, requiring (besides the catalyst) only CO and $H_2$, and (3) they are operationally simple (requiring only an initial investment in the high pressure apparatus)—a quick filtration through a plug of silica to remove the catalyst comprises the work-up and purification procedure.

Catalyst variation and substrate variation is also important. Variation of the catalyst may focus on the phosphine ligands. Many different triarylphosphines are available with both electron withdrawing and electron donating substituents attached to the aromatic rings. The steric properties of the phosphine ligands will be affected as well by the presence of ortho substituents. These may be screened in the hydroformylation as may trialkyl phosphines and chelating diphosphines (see, for example, FIG. 1B, where $R^1$ is Me and $R^2$ is t-Bu). In addition, all other relevant reaction variables may be varied including temperature, solvent, and total pressure of CO:$H_2$ as the two competing pathways might very well have different responses to such changes.

Figure 7:
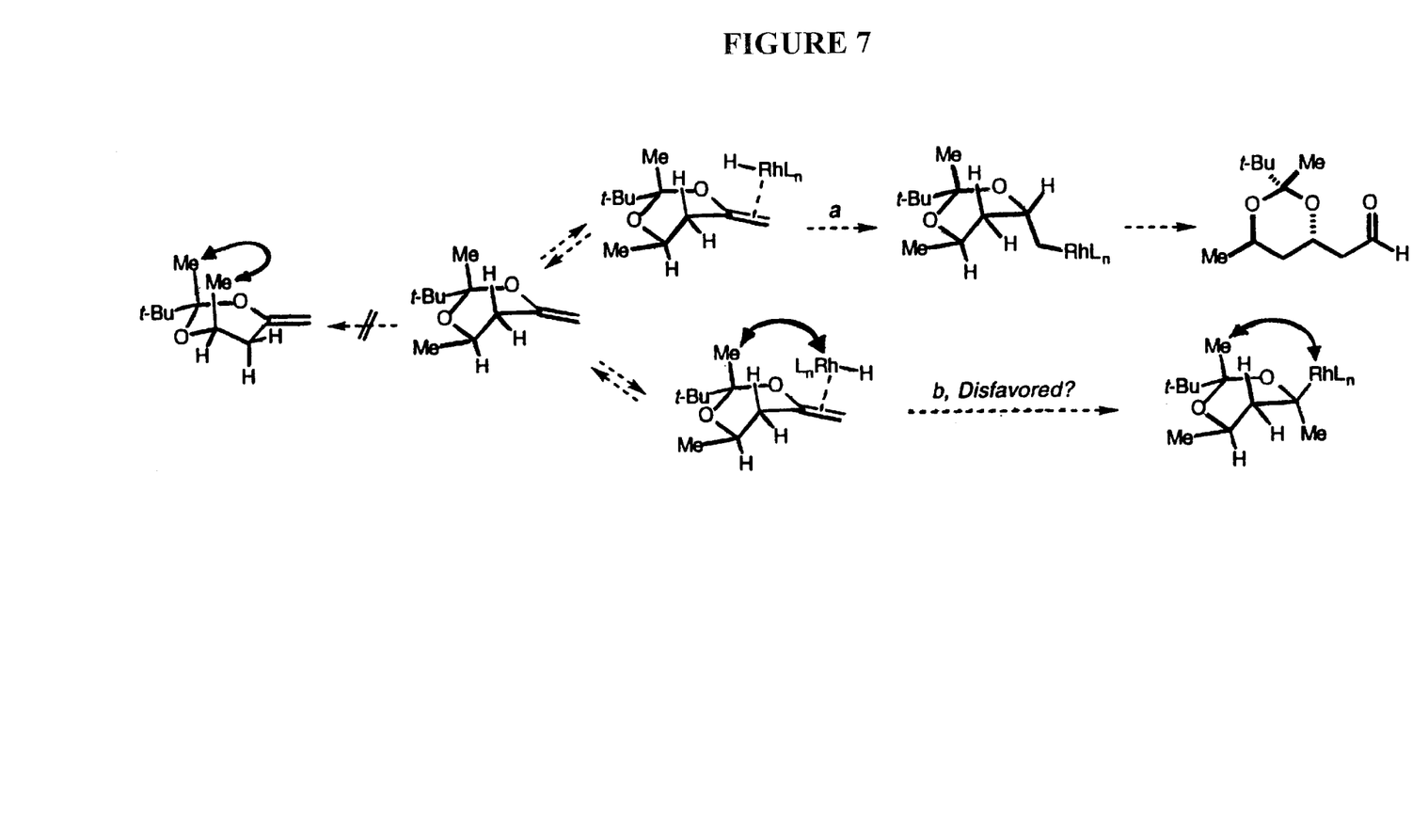
FIG. 7. Mechanistic model for the hydroformylation reaction indicating potential affects of the addition of an axial methyl or other substituent at the acetyl carbon position.

Variation of the substrate includes varying the acetal groups. The addition of an axial methyl or other substituent at the acetal carbon may (1) completely lock in the boat conformation of the substrate and (2) sterically inhibit attachment of the rhodium to the internal carbon of the olefin, effectively shutting down the isomerization pathway (FIG. 7). Thus, targetting the pinacolone-derived acetal A, (b) may be significantly inhibited, while the desired hydroformylation pathway (a) will be little affected. An additional feature of this boat-like conformational model is that substituents other than methyl should be readily tolerated at the 6-position of the 4-methylene-1,3-dioxane.

Figure 8:
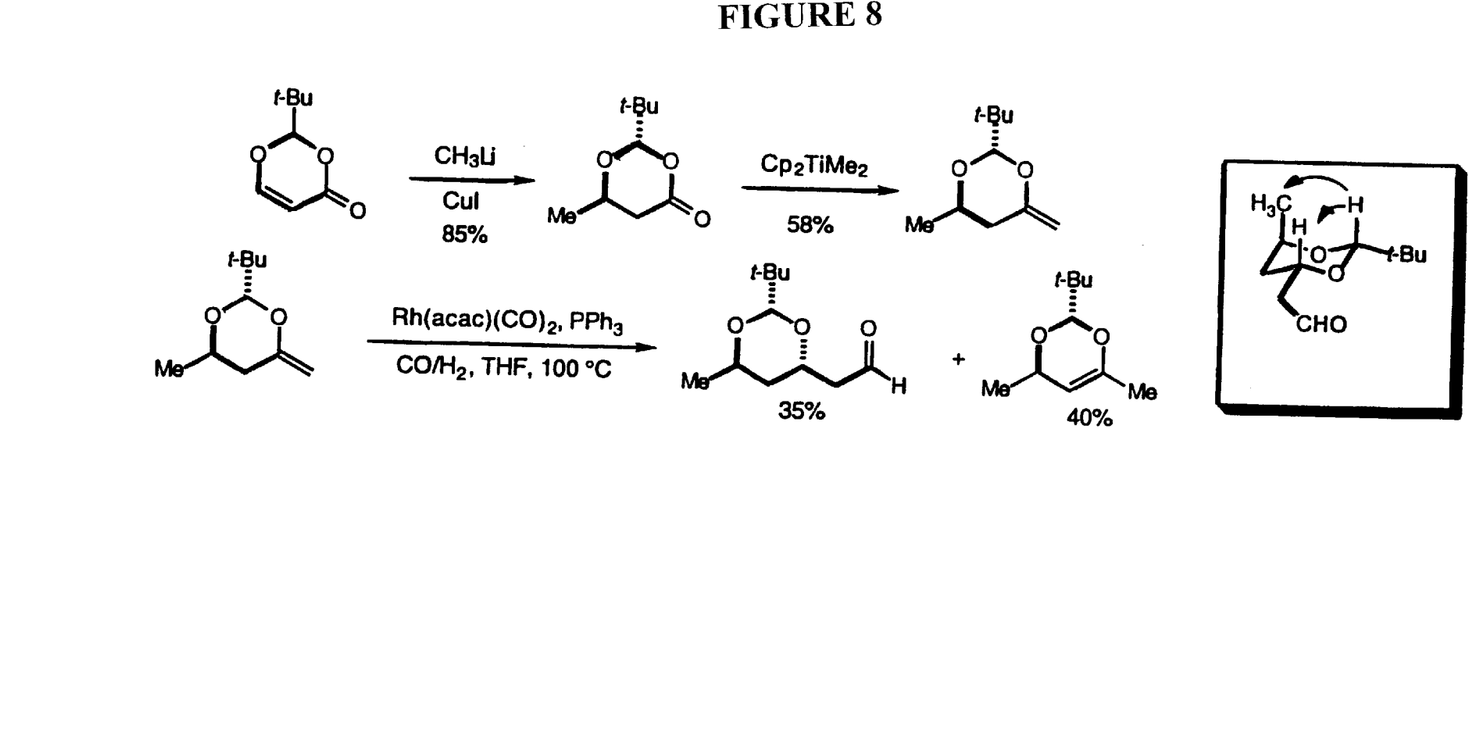
FIG. 8. Dioxinone-cuprate addition strategy in the presence of an axial group in the acetyl position; hydroformylation and resulting products.
Figure 9:
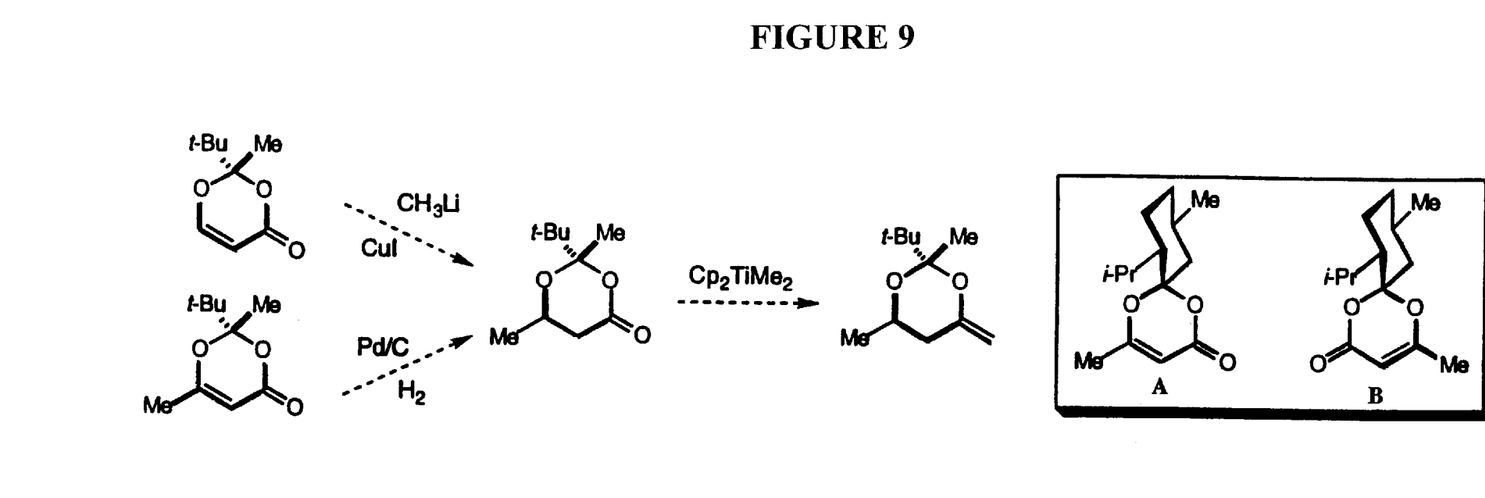
FIG. 9. Hydrogenation of 6-substituted 1-3-dioxin-4-ones.

A variety of ketone-derived acetals including chiral ketone-derived acetals, may be used. This requires a diastereoselective synthesis of such acetals. The dioxinone-cuprate addition strategy of Seebach, used in the preparation of the terminal olefin in FIG. 8, may be effective even in the presence of an axial group at the acetal position (see FIG. 9). Seebach has argued that the diastereoselectivity in these reactions is a result of pyramidalization of the β-carbon of the unsaturated lactone, and not steric factors. (Seebach, 1988). However, the addition of an axial substituent is a non-trivial change and could render this strategy ineffective. Alternatively, hydrogenation of 6-substituted 1,3-dioxin-4-ones is performed. (FIG. 9). Importantly, such compounds are readily available. Indeed, diastereomers A and B of FIG. 9 are known compounds available in enantiomerically pure form in one step from simple starting materials. (Demuth, et al., 1986). These latter compounds can be hydrogenated and then methylenated for use in the hydroformylation process.

The focus of the present invention is on selection of substrates which give the highest regioselectivity balanced against the fastest rate. Although hydroformylations of vinyl ethers and vinyl esters are known, this invention provides the first examples of hydroformylation of α-substituted vinyl ethers, acetals or esters. This is an important distinction, as vinyl ethers and esters both produce predominantly the branched, α-oxygenated aldehydes in rhodium-catalyzed hydroformylation. (Lazzaroni, et al., 1983; Amer, et al., 1990; Polo, et al., 1992a; Polo, et al., 1992b; Kollar, et al., 1993; Lazzaroni, et al., 1995). The chemistry presented herein has already demonstrated that this electronic preference is overridden—presumably for steric reasons—by an α-substituent and that a reasonable rate can still be achieved, at least with cyclic enol acetals. Whether this effect will translate to simple acyclic enol ethers, acetals and esters must be determined experimentally. The cyclic counterparts may be prepared and hydroformylated in order to understand the separate steric and electronic contributions to the observed regioselectivity. It is important to analyze various phosphine and phosphite ligands with each substrate. Not only monodentate ligands, but chelating diphosphines and diphosphites can be examined. It has demonstrated that the bite angle of chelating diphosphines has dramatic effect on hydroformylation regiochemistry. (Casey, et al., 1992).

When substrate/ligand combinations are identified, the process of selecting/designing effective chiral ligands may proceed. Many chiral $C_2$-symmetric diphosphines are known and have been tested in asymmetric hydroformylation. (Agbossou, et al., 1995). The most successful ligand, however, is the non-$C_2$-symmetric mixed phosphine phosphite BINAPHOS ligand which induces enantiomeric excesses over 90% in the hydroformylation of many monosubstituted olefins and some styrene derivatives. (Sakai, et al., 1993). Moderate enantioselectivity in styrene hydroformylation has been achieved by researchers at Union Carbide (Babin and Whiteker, 1992) and van Leeuwen (Buisman, et al., 1995) using $C_2$-symmetric diphosphites derived from simple chiral diols. Interestingly, larger ring chelates gave higher enantioselectivities by enforcing a bis-equitorial binding on the trigonal bipyramidal rhodium center, whereas the BINAPHOS ligands are believed to bind in an axial-equitorial fashion. These and other known ligands can be synthesized and tested for enantioselectivity with the substrates discussed above. Based on the results of the initial screening of known chiral ligands, development of a model for those factors which lead to enantioselective hydroformylation of the selected substrates may proceed. Such a model can guide the design of new ligands. Indeed, the requirements for selective attachment of the rhodium to a prochiral monosubstituted olefinic carbon are potentially distinct from the requirements for selective attachment of the hydride to a prochiral disubstituted olefinic carbon.

REFERENCES

Agbossou, F.; Carpentier, J.-F.; Mortreux, A. 1995. Asymmetric Hydroformylation, Chem. Rev. 95, 2485–2506.

Amer, I.; Alper, H. 1990. Zwitterionic Rhodium Complexes as Catalysts for the Hydroformylation of olefins, J. Am. Chem. Soc. 112, 3674–3676.

Beller, M.; Cornils, B.; Frohning, C. D.; Kohlpaintner, C. W. 1995. Progress in Hydroformylation and Carbonylation, J. Mol. Catal. A, 104, 17–85.

Bolard, J. 1986. How do the polyene macrolide antibiotics affect the cellular membrane properties? Biochim. Biophys. Acta, 864, 257–304.

Botteghi, C.; Ganzerla, R.; Lenarda, M.; Moretti, 1987. Advances in the Hydroformylation of Olefins Containing Functional Groups, G. J. Mol. Catal. 40, 129–182.

Buisman, G. J. H.; Vos, E. J.; Kamer, P. C. J.; van Leeuwen, P. W. N. M. 1995. Hydridorhodium Diphosphite Catalysts in the Asymmetric Hydroformylation of Styrene, J. Chem. Soc., Dalton Trans. 409–417.

D'Ambrosio, M.; Guerriero, A.; Debitus, C.; Pietra, F. 1996. 6. Leucascandrolide A, a New Type of Macrolide: the First Powerfully Bioactive Metabolite of Calcareous Sponges (*Leucascandra caveolata*, a New Genus from the Coral Sea), *Helv. Chim. Acta* 79, 51–60.

Demuth, M.; Palomer, A.; Sluma, H.-D.; Dey, A. K.; Kruger, C.; Tsay, Y.-H. 1986. Asymmetric Photocycloadditions with Optically Pure, Spirocyclic Enones. Simple Synthesis of (+)- and (−)-Grandisol, *Angew. Chem., Int. Ed. Engl.* 25, 1117–1119.

Casey, C. P.; Whiteker, G. T.; Melville, M. G.; Petrovich, L. M.; Gavney, Jr., J. A.; Powell, D. R. 1992. Diphosphines with Natural Bite Angles near 120; Increase Selectivity for n-Aldehyde Formation in Rhodium-Catalyzed Hydroformylation, *J. Am. Chem. Soc.* 114, 5535–5543.

H. M. Colquhoun, D. J. Thompson, and M. V. Twigg. 1991. Carbonylation: Direct Synthesis of Carbonyl Compounds, Plenum Press: New York.

Hartsel, S. C.; Hatch, C.; Ayenew, W. 1993. How Does Amphotericin B Work?: Studies on Model Membrane Systems, *J. Liposome Res.* 3, 377–408.

J. E. Babin and G. T. Whiteker, Pat., WO 93/03830, 1992.

Jongsma, T.; Challa, G.; Van Leeuwen, P. W. N. M. 1991. A Mechanistic Study of Rhodium tri(o-t-butylphenyl) phosphite complexes as Hydroformylation Catalysts, *J. Organomet. Chem.* 421, 121–128.

Kennedy, R. M.; Abiko, A.; Takenasa, T.; Okumoto, H.; Masamune, S. 1988. A Synthesis of 19-Dehydroamphoteronolide B, *Tetrahedron Lett.* 29, 451–454.

Kollar, L.; Sandor, P. 1993. Highly Stereoselective Hydroformylation of a (2R)-2-tert-butyl-D$^4$-1,3-oxazoline Derivative, *J. Organomet. Chem.* 445, 257–259.

Lazzaroni, R.; Settambolo, R.; Uccello-Barretta, G. 1995. b-Hydride Elimination and Regioselectivity in the Rhodium-Catalyzed Hydroformylation of Open Chain Unsaturated Ethers, *Organometallics*, 14, 4644–4650.

Lazzaroni, R.; Pucci, S.; Bertozzi, S.; Pini, D. 1983. Diastereoselectivity in the Rhodium-Catalyzed Hydroformylation of (+)(R)-1-Phenylethyl Vinyl Ether, *J. Organomet. Chem.* 247, C56–C58.

Mori, Y.; Asai, M.; Kawade, J.; Okumura, A.; Furukawa, H. 1994. Total Synthesis of the Polyene Macrolide Roxaticin, *Tetrahedron Lett.* 35, 6503–6506.

Nicolaou, K. C.; Daines, R. A.; Ogawa, Y.; Chackraborty, T. K. 1988. Total Synthesis of Amphotericin B. 3. The Final Stages, *J. Am. Chem. Soc.* 110, 4696–4705.

Oishi, T.; Nakata, T. 1990. New Aspects of Stereoselective Synthesis of 1,3-Polyols, *Synthesis* 635–645.

Petasis, N. A.; Lu, S. -P. 1996. Stereocontrolled Synthesis of Substituted Tetrahydropyrans from 1,3-Dioxan-4-ones, *Tetrahedron Lett.* 37, 141–144.

Polo, A.; Claver, C.; Castill-n, S.; Ruiz, A.; Bay-n, J. C.; Real, J.; Mealli, C.; Masi, D. 1992. Regioselective Hydroformylation of Cyclic Vinyl and Allyl Ethers with Rhodium Catalysts. Crucial Influence of the Size of the Phosphorus Cocatalyst, *Organometallics* 11, 3525–3533.

Polo, A.; Fernandez, E.; Claver, C.; Castill-n. 1992. Hydroformylation of Glucal Derivatives with Rhodium Catalysts. Crucial Influence of the Auxiliary Ligand Tris (ortho-tert-butylphenyl) Phosphite, *S. J. Chem. Soc., Chem. Commun.* 639–640.

Poss, C. S.; Rychnovsky, S. D.; Schreiber, S. L. 1993. Two-Directional Chain Synthesis: An Application to the Synthesis of (+)-Mycoticin A, *J. Am. Chem. Soc.* 115, 3360–3361.

Rychnovsky, S. D.; Hoye, R. C. 1994. Convergent Synthesis of the Polyene Macrolide (−)-Roxaticin, *J. Am. Chem. Soc.* 116, 1753–1765.

Rychnovsky, S. D. 1995. Oxo Polyene Macrolide Antibiotics, *Chem. Rev.* 95, 2021–2040.

Rychnovsky, S. D.; Khire, U. R.; Yang, G. 1997. Total Synthesis of the Polyene Macrolide Roflamycoin, *J. Am. Chem. Soc.* 119, 2058–2059.

Sakai, N.; Mano, S.; Nozaki, K.; Takaya, H. 1993. Highly Enantioselective Hydroformylation of Olefins Catalyzed by New Phosphinephosphite-Rh(I) Complexes, *J. Am. Chem. Soc.* 115, 7033–7034.

Seebach, D.; Imwinkelried, R.; Stucky, G. 1987. Optisch aktive Alkohole aus 1,3-Dioxan-4-onen: eine praktikable Variante der enantioselectiven Synthese unter nucleophiler Substitution an Acetal-Zentren, *Helv. Chim. Acta*, 70, 448–464.

Seebach, D.; Zimmerman, J.; Gysel, U.; Ziegler, R.; Ha, T.-K., 1988. Totally Stereoselective Additions to 2,6-Disubstituted 1,3-Dioxin-4-ones (Chiral Acetoacetic Acid Derivatives). Synthetic and Mechanistic Aspects of Remote Stereoselectivity. *J. Am. Chem. Soc.* 110, 4763–4772.

Sternberg, S. 1994. The Emerging Fungal Threat, *Science* 266, 1632–1634.

Van Leeuwen, P. W. N. M.; Roobeek, C. F. 1983. Hydroformylation of Less Reactive Olefins with Modified Rhodium Catalysts, *J. Organomet. Chem.* 258, 343–350.

Yamamoto, Y.; Asao, N. 1993. Selective Reactions Using Allylic Metals, *Chem. Rev.* 93, 2207–2293.

What is claimed is:

1. A process for producing an optically active aldehyde represented by the formula:

[chemical structure]

comprising hydroformylation of a terminal olefin substrate represented by the formula:

[chemical structure]

wherein $R^1$ represents isopropyl, methyl, $BnO(CH_2)_2$, or $(CH_3)_2C{=}C(CH_2)_5$ and $R^2$ represents t-butyl or methyl group; in the presence of CO, $H_2$ and a catalyst, which catalyst comprises a transition metal based compound and a ligand.

2. The process of claim 1, wherein the ligand is a phosphine.

3. The process of claim 2, wherein the phosphine is $PPh_3$.

4. The process of claim 1, wherein the transition metal based compound comprises rhodium.

5. The process of claim 4, wherein the transition metal based compound is $Rh(acac)CO_2$.

6. The process of claim 1, wherein the hydroformylation is performed in an ethereal solvent.

7. The process of claim 5, wherein the ethereal solvent is tetrahydrofuran.

8. A process for producing an optically active aldehyde comprising hydroformylation of 4-methylene-1,3-dioxane in the presence of CO, $H_2$ and a catalyst, which catalyst comprises a transition metal based compound and a ligand.

9. The process of claim 8, wherein the ligand is a phosphine.

10. The process of claim 9, wherein the phosphine is $PPh_3$.

11. The process of claim 8, wherein the transition metal based compound comprises rhodium.

12. The process of claim 11, wherein the transition metal based compound is $Rh(acac)CO_2$.

13. The process of claim 8, wherein the hydroformylation is performed in an ethereal solvent.

14. The process of claim 13, wherein the ethereal solvent is tetrahydrofuran.

\* \* \* \* \*